United States Patent
Mahó et al.

(10) Patent No.: US 11,274,119 B2
(45) Date of Patent: Mar. 15, 2022

(54) INDUSTRIAL PROCESS FOR THE SYNTHESIS OF NOMEGESTROL-ACETATE

(71) Applicant: RICHTER GEDEON NYRT., Budapest (HU)

(72) Inventors: Sándor Mahó, Budapest (HU); János Csörgei, Budapest (HU); Csaba Sánta, Budapest (HU); Péter Vincze, Kóka (HU); László Balogh, Budapest (HU); János Horváth, Budapest (HU); Zoltán Béni, Maglód (HU)

(73) Assignee: Richter Gedeon Nyrt., Budapest (HU)

( * ) Notice: Subject to any disclaimer, the term of this patent is extended or adjusted under 35 U.S.C. 154(b) by 349 days.

(21) Appl. No.: 16/463,425

(22) PCT Filed: Dec. 15, 2017

(86) PCT No.: PCT/HU2017/050057
§ 371 (c)(1),
(2) Date: May 23, 2019

(87) PCT Pub. No.: WO2018/109508
PCT Pub. Date: Jun. 21, 2018

(65) Prior Publication Data
US 2021/0115084 A1    Apr. 22, 2021

(30) Foreign Application Priority Data
Dec. 16, 2016    (HU) .................................. P1600671

(51) Int. Cl.
*C07J 75/00* (2006.01)
*C07J 7/00* (2006.01)

(52) U.S. Cl.
CPC ............. *C07J 75/00* (2013.01); *C07J 7/0045* (2013.01)

(58) Field of Classification Search
CPC .............................. C07J 75/00; C07J 7/0045
See application file for complete search history.

(56) References Cited

U.S. PATENT DOCUMENTS 4,544,555 A    10/1985    Gastaud

FOREIGN PATENT DOCUMENTS

| AU | 635739 B2 | 4/1993 | | |
| CN | 102952169 A | 3/2013 | | |
| WO | WO-9012027 A1 * | 10/1990 | ............... | C07J 9/00 |
| WO | 2006/077209 A1 | 7/2006 | | |
| WO | 2014/067127 A1 | 5/2014 | | |

OTHER PUBLICATIONS

Lu et al.: "An Improved Synthesis of Nomegestrol Acetate", Organic Process Research & Development, 2014, vol. 18, pp. 431-436.

* cited by examiner

*Primary Examiner* — Susanna Moore
(74) *Attorney, Agent, or Firm* — Jason D. Voight

(57) ABSTRACT

The invention relates to the last step of a synthetic process, in which Nomegestrol-acetate of formula (I) is synthesized from 17α-acetoxy-6-methylene-19-norpregn-4-ene-3,20-dione of formula (II) in the presence of Pd/C catalyst and acetic acid in hot ethanolic solution.

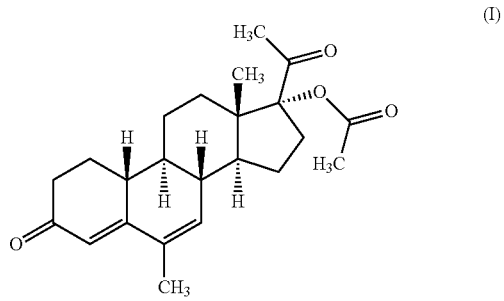

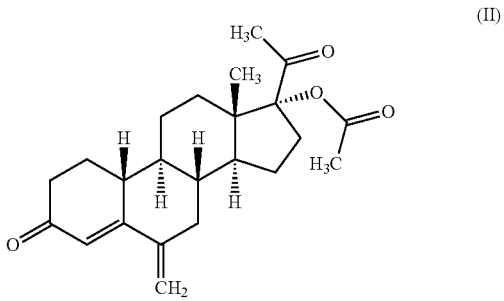

7 Claims, No Drawings

INDUSTRIAL PROCESS FOR THE SYNTHESIS OF NOMEGESTROL-ACETATE

This is the national stage of International Application PCT/HU2017/050057, filed Dec. 15, 2017.

FIELD OF THE INVENTION

The invention relates to a process for the synthesis of 17α-acetoxy-6-methyl-19-norpregna-4,6-diene-3,20-dione (Nomegestrol-acetate) of formula (I)

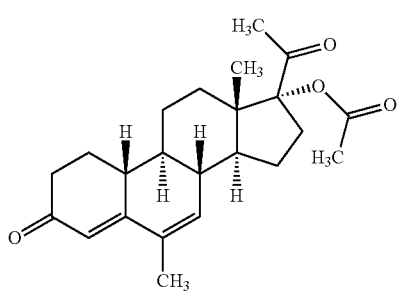

starting from 17α-acetoxy-6-methylene-19-norpregn-4-ene-3,20-dione of formula (II).

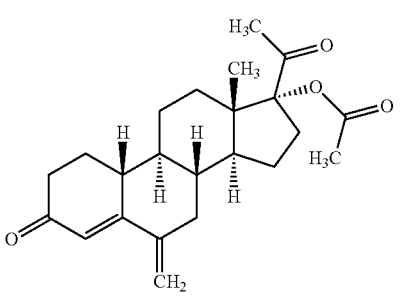

17α-acetoxy-6-methyl-19-norpregna-4,6-diene-3,20-dione of formula (I) (Nomegestrol-acetate) is a highly potent orally active progestogen, which possess excellent antigonadotropic properties, and binds specifically to the progesterone receptor. Due to its favorable metabolism and pharmacological properties it is used in oral hormonal contraceptives and in several gynecological therapies (menstrual disorders, painful menstruation, premenstrual syndrome, HRT/hormone replacement therapy, menopausal symptoms, diseases of uterus and increased menstruation).

BACKGROUND OF THE INVENTION

According to the literature only one method is known for the synthesis of Nomegestrol-acetate of formula (I) from 17α-acetoxy-6-methylene-19-norpregn-4-ene-3,20-dione of formula (II), in this method compound of formula (II) is converted to compound of formula (I) in primary alcohols, or in a mixture of solvents containing primary alcohols (preferably ethanol) at a temperature between 50° C. and the boiling point of the solvent, using palladium/carbon catalyst and different auxiliary materials (sodium acetate, water, cyclohexene).

The patent GB 1,515,284 describes the synthesis of Nomegestrol-acetate of formula (I) starting from 17α-acetoxy-6-methylene-19-norpregn-4-ene-3,20-dione of formula (II). The isomerization reaction was carried out in a volume of two hundred fold ethanol calculated on the amount of the steroid at boiling temperature, using 50 weight % of sodium acetate and 100 weight % of Pd/C over a period of 1.5 h. After work up of the reaction mixture by extraction and crystallization from methanol the product was obtained in 60% yield (mp: 178° C.). The purity of the product was not given.

According to the paper published in Org. Process Res. Dev. 2014, 18, 431-436 by Chinese authors the isomerization reaction of 17α-acetoxy-6-methylene-19-norpregn-4-ene-3,20-dione of formula (II) contrary to the patent GB 1,515,284 was carried out in a mixture of solvents containing 7.1 fold tetrahydrofuran and 1.4 fold ethanol calculated on the amount of the steroid using 100 weight % of 5% Pd/C catalyst, which contained 54% of water and the reaction mixture was refluxed for 45 min. The product was obtained in a yield of 77% after crystallization from a mixture of petrol ether and ethyl acetate. According to HPLC the purity of the product was >99.8% (187 nm) and 99.4% (254 nm), melting point: 214-215° C.

The HPLC method described in the Ph. Eur. pharmacopeia for the determination of the purity of Nomegestrol-acetate summarizes two results of the purity of the product measured specifically at 245 nm (wavelength characteristic for the main impurities) and 290 nm (wavelength characteristic for NOMAC and nomegestrol). The Chinese publication does not describe the HPLC method used by them, only the two wavelength of the measurement, but those are not identical with the ones given in the pharmacopeia. Due this facts, it is not obvious whether the purity of the product obtained by the Chinese authors fulfills the requirements of the Ph. Eur. pharmacopeia.

Furthermore in the Chinese paper the isomerization reaction is described only at a labor scale, and it is not applicable on an industrial scale. They do not give a detailed method for the purification of the crude product either, only mention a recrystallization using a mixture of petrol ether and ethyl acetate as solvent. On an industrial scale petrol ether is not applicable because of safety reasons.

When repeating the reaction according to the description, we found that the obtained product contained far more impurities and the yield (58%) was lower than written in the paper. In the crude product the amount of the dimer-2 impurity was 4.2%, whereas the amount of the dimer-1 impurity was 2.6%.

According to the WO2014/067127 (A1) patent application the isomerization reaction was carried out the following way: the 17α-acetoxy-6-methylene-19-norpregn-4-ene-3,20-dion of formula (II) was submitted to isomerization without drying. Approximately three fold ethanol, 62.5 weight % of 5% Pd/C catalyst, which contained 54% of water and 0.625 weight % of cyclohexene were used calculated on the amount of the wet steroid and the reaction mixture was stirred at a temperature of 25-80° C. for 2-4 hours. The product was purified by chromatography using petrol ether and ethyl-acetate as solvent. In the description neither the yield nor the purity is given for the isomerization step.

In the Chinese patent application CN102952169 examples given for the isomerization reaction are identical to those of the WO2014/067127 patent application.

In the experimental examples as well in the claims of the patent application the 3-ethoxy-6-methylene-17α-acetoxy-19-norpregna-3,5-diene-20-one is given as the starting material in all the five examples. In our patent application in contrary to this the isomerization is carried out using 17α-acetoxy-6-methylene-19-norpregn-4-ene-3,20-dione of formula (II) as starting compound. In contrary to our patent application they carry out the isomerization in the presence of cyclohexene.

In the patent application WO2006/077209 (A1) the synthesis of medrogeston is described starting from 17α-methyl-6-methylene-pregn-4-ene-3,20-dione by an isomerization reaction using palladium as catalyst. The reaction was carried out on a kg scale using 5% Pd/C catalyst (0.2 fold of the weight of the steroid) suspended in a 10 fold volume of ethanol, calculated on the weight of the steroid. The steroid is added to the suspension heated to its boiling point. After the completion of the reaction (1.5-3 hours) the catalyst is removed by filtration, washed with ethanol and the volume of the obtained solution of the steroid is concentrated to the six fold of the amount of the steroid by evaporation. Fourfold amount of water is added to the mixture, which is then cooled to room temperature. The crystals are filtered and dried in vacuum. The crude product is stirred in ethanol at the boiling point, cooled to room temperature, and the crystals are filtered and dried. The yield is 80.5%. The purity is not given.

DESCRIPTION OF THE INVENTION

The steroids containing a 19-norpregnan skeleton behave differently in their chemical reactions compared to the corresponding steroids containing a pregnane skeleton, due to the lack of the methyl group at position 10. Their physical properties, stabilities are less advantageous and during their chemical reactions, using identical conditions, significantly more side-reaction will occur, compared to the steroids having a pregnane skeleton. This effect is particularly strong in those cases, when the planned chemical transformations take place in the vicinity of the A- and B-ring of the steroid.

According to our experience this problems prevail even stronger in the case of 6-methylene-gestonoron-acetate of formula (II). While reproducing the methods described in the literature for the synthesis of Nomegestrol-acetate we found, that the steroid of formula (II) in solution—mainly at higher temperatures—undergoes a decomposition yielding typical side-products. We isolated the two main decomposition products, determined their structure and identified them as dimer isomers, which are formed via a Diels-Alder reaction.

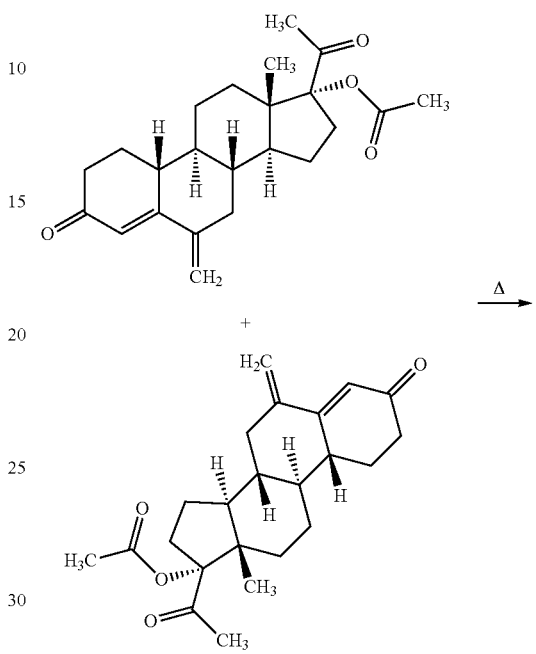

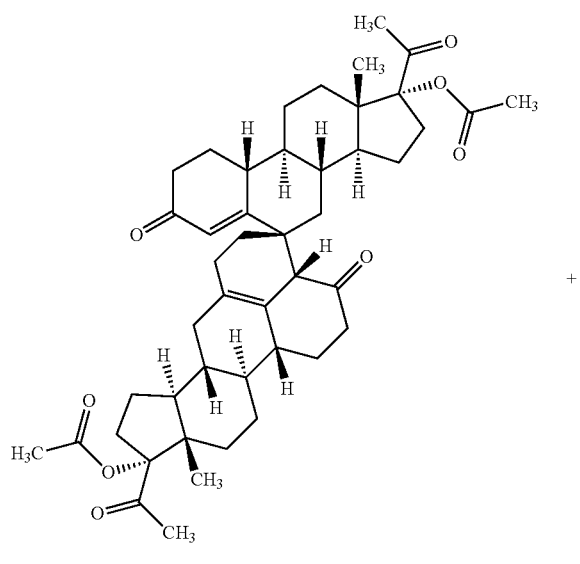

dimer-1

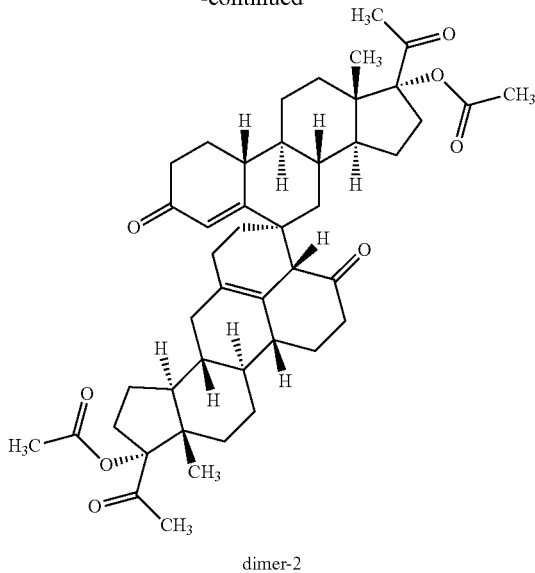

dimer-2

We did not observe earlier such type of decomposition either in the case of the steroids carrying the pregnane skeleton or in the case of the 19-nor-steroids and did not find the description of such a decomposition in the literature. We investigated the reasons leading to the formation of these dimers as well as the possibilities of decreasing their formation. According to our experiments, in the case of the steroids having similar structural elements but a pregnane skeleton such Diels-Alder type dimerizations do not take place, consequently the presence or the absence of the methyl group at position 19 is responsible for the different chemical behavior of these two type of steroids.

During our experiments surprisingly we found, that the aforementioned disadvantages did not occur when the starting steroid was added in solid state into the hot ethanolic suspension of the Pd/C catalyst. In this case the starting material was immediately dissolved and was converted in a few minutes into the product. Due to the fast reaction the possibility of the dimerization was reduced considerably. The fast reaction had a beneficial effect on the amount of the other by-products (reduced, or dehydrogenated—aromatic—compounds and hydrolyzed by-products), which are formed due to the influence of the Pd/C catalyst. The advantages of the fast reaction are especially appear, when the catalyst is also filtered out quickly, as otherwise the redox and hydrolytic side-reactions providing the by-products still go on. This causes problems mainly when the reaction is scaled up, as the amount of the by-products formed depending on the activity of the catalyst can not be predicted. According to our experiments these problems can be solved by giving a small amount of acetic acid to the reaction mixture. With the addition of acetic acid an advantageous pH value can be reached, influencing the feature of the catalysts of different activity and basicity.

During our work surprisingly it was found that, as compared to the syntheses described in the literature, we can produce Nomegestrol-acetate active ingredient meeting the necessary high standards of the pharmaceutical industry, using a more simple and more economical way by applying an inert atmosphere, and adding the solid 6-methylene-gestonoron-acetate of formula (II) into 10-100 fold, preferably 20-40 fold volume ethanol solution at 50-78° C., preferably at 70-78° C., which contains 0.05-0.2 mass fraction, preferably 0.08-0.2 mass fraction of 10% Pd/C catalyst, and 0.01-0.2 mass fraction, preferably 0.03-0.07 mass fraction of acetic acid calculated on the weight of the steroid, then, after 3-15 min, preferably after 5-10 min, the catalyst is filtered off from the hot solution, the filtrate is concentrated to a 10-fold volume (calculated also on the weight of the steroid) and 20-30-fold water is added, the precipitated product is filtered off and washed neutral with water. The crude product is purified by suspending it in a mixture of 2.8-fold acetone and 2.8-fold water.

Advantages of the process described in the present invention are:
  the isomerization reaction can be carried out in primary alcohols (preferably ethanol) in the presence of a Pd/C catalyst
  for the synthesis on an industrial scale it is not necessary to use from the point of safety dangerous solvents, such as e.g. petrol ether
  there is no solvent mixture present in the method, which is beneficial both from the environmental as well as the industrial point of view
  the discovery of the phenomena of dimerization, the identification of the dimeric impurities and keeping them on a safe low level (in connection with the reversed addition), as well as
  tuning the activity of the catalyst by acetic acid, due to which the amount of the critical impurities can be minimalized, and the robustness of the reaction can be ensured during the scale up.
  the high yield (90.2%) achieved in plant-size batches, the pharmacopeia quality of the product (the amount of impurities already in the crude product is so low, that it can be converted into an active ingredient of a drug by applying a simple treatment with a mixture of acetone and water instead of chromatographic purification)
  the Pd/C catalyst is used in small amount as compared to the known procedures
  we apply a short reaction time, therefore the total amount of impurities in the crude product remains low
  the technology of the procedure is simple, safe, fast, economic, can be applied on an industrial scale and can easily be scaled up.

The advantages of the procedure worked out by us and mentioned above made possible to produce Nomegestrol-acetate in a quality suitable to use as active ingredient by avoiding the generally applied expensive chromatographic purification step and using a relatively simple, acetone-water treatment.

EXAMPLES

Example 1

Synthesis of 17α-acetoxy-6-methyl-19-norpregna-4,6-diene-3,20-dione of Formula (I)

Under nitrogen 1.0 g of 10% Pd/C catalyst and 0.5 cm³ of acetic acid was added at 20-25° C. to 400 cm³ of ethanol. The mixture was heated to 72-75° C., then 10.0 g of 17α-acetoxy-6-methylene-19-norpregna-4-ene-3,20-dione of formula (II) steroid was added. The reaction mixture was stirred for 10 minutes at 72-75° C., then the catalyst was filtered off. The solution of the steroid was concentrated in vacuum to a volume of 100 cm³ and 250 cm³ water was added. The formed slurry of crystals was cooled to 0-5° C., and was stirred at this temperature for one hour. Thereafter the crystals were filtered off and washed with water till neutrality. According to HPLC this crude product contained 0.04% of dimer-1 and 0.14% of dimer-2 impurities. 28 cm$^3$ of acetone was added to the wet crude product, the so obtained slurry was stirred for 2 minutes at 20-25° C., then 28 cm$^3$ of water was added. This slurry of the crystals was stirred for 15 minutes, cooled to 0-5° C. and stirring was continued at this temperature for 1 hour. The crystals were filtered, washed with 47 cm$^3$ of water and the product was dried in vacuum.

Product: 8.7 g (87%), ≤0.3% of total impurities.

$[\alpha]_D^{25}$=−60.4° (c=2%, EtOH)

$^1$H NMR (CDCl$_3$, 799.7 MHz) δ: 6.04 (s, 1H), 5.96 (s, 1H), 3.00 (ddd, J=15.9, 11.3, 2.2 Hz, 1H), 2.49-2.62 (m, 1H), 2.27-2.38 (m, 3H), 2.11-2.17 (m, 1H), 2.10 (s, 3H), 2.06 (s, 3H), 2.02 (td, J=13.0, 4.4 Hz, 1H), 1.87-1.97 (m, 3H), 1.86 (dd, J=1.9, 1.1 Hz, 3H), 1.79-1.85 (m, 1H), 1.53-1.62 (m, 2H), 1.38-1.48 (m, 1H), 1.34 (qd, J=13.1, 4.1 Hz, 1H), 1.15-1.24 (m, 1H), 0.65-0.76 (m, 3H)

$^{13}$C NMR (CDCl$_3$, 201.1 MHz) δ: 203.9, 200.4, 170.6, 159.3, 139.5, 132.3, 121.8, 96.5, 48.6, 47.4, 45.5, 41.0, 41.0, 37.5, 30.9, 30.2, 26.9, 26.4, 24.9, 23.1, 21.2, 19.3, 14.2

HRMS: 371.22170 (C$_{23}$H$_{13}$O$_4$; calc. 371.22169). ESI-MS-MS (rel. int %, cid=35%): 311(100); 293(12); 275(3); 269(4); 267(2); 251(7); 235(2); 209(7).

The quality of the product meets the requirements of the Ph. Eur pharmacopeia.

Example 2

Synthesis of 17α-acetoxy-6-methyl-19-norpregna-4,6-diene-3,20-dione of Formula (I) on a Pilot Plant Scale Under nitrogen 0.4 kg of 10% Pd/C catalyst and 0.2 liter of acetic acid was added to 160 liter of ethanol. The mixture was heated to 72-75° C., then 4 kg of 17α-acetoxy-6-methylene-19-norpregna-4-ene-3,20-dione of formula (II) steroid was added using a powder feeder. The reaction mixture was stirred at 72-75° C. for 10 minutes, then the catalyst was filtered off. The solution of the steroid was concentrated in vacuum to a volume of 40 liter and 100 liter of water was added. The obtained slurry of crystals was cooled to 0-5° C., and it was stirred at this temperature for one hour. Thereafter the crystals were filtered off and washed with water till neutrality. According to HPLC the wet product contains 0.02% of dimer-1 and 0.08% of dimer-2 impurities. 11.2 liter of acetone was added to the wet product, the obtained slurry was stirred at 20-25° C. for 5 minutes and thereafter 11.2 liter of water was added. The slurry of crystals was stirred for 15 minutes, then cooled to 0-5° C. and stirring was continued at this temperature for 1 hour. The crystals were filtered off, washed with 18.8 liter of water and the product was dried in vacuum.

Product: 3.61 kg (90.2%), ≤0.3% of total impurities (dimer-1: ≤DL, dimer-2: 0.02%)

Example 3 (an Example Comparing the Dimer Impurities)

Synthesis of 17α-acetoxy-6-methyl-19-norpregna-4,6-diene-3,20-dione of formula (I)

(the starting material is added first into the reaction mixture at 20-25° C.) Under nitrogen 1.0 g of 10% Pd/C catalyst and 0.5 cm$^3$ of acetic acid was added to 400 cm$^3$ of ethanol at 20-25° C., then 10.0 g of 17α-acetoxy-6-methylene-19-norpregna-4-ene-3,20-dione of formula (II) steroid was added to the reaction mixture at 20-25° C. The reaction mixture was heated to 72-75° C., and stirred at this temperature until completion of the reaction, then the catalyst was filtered off. The solution of the steroid was concentrated in vacuum to a volume of 100 cm$^3$ and 250 cm$^3$ of water was added. The obtained slurry of crystals was cooled to 0-5° C., stirred at this temperature for one hour, then filtered off, washed with water till neutrality and dried. According to HPLC the crude product contained 1.7% of dimer-1 and 5.7% of dimer-2 impurities.

Example 4

Synthesis of the Diels-Alder Dimer Products

A solution of 5 g of 17α-acetoxy-6-methylene-19-norpregn-4-ene-3,20-dione in 80 ml of toluene was refluxed under nitrogen for 12 hour. The solution was concentrated under diminished pressure and the solid residue was recrystallized from ethyl acetate to yield after drying 2.5 g of a product, which according to structure elucidation was (3R,3aS,5aS,5bR,8'R,8aR,9S,9'S,10'R,12aR,12bS,13'S,14'S,17'R)-3,17'-diacetyl-3a,13'-dimethyl-3',8-dioxo-1',2,2',3,3',3a,4,5,5a,5b,6,7,7',8,8',8a,9',10,10',11,11',12,12',12a,12b,13',14',15',16',17'-triacontahydro-1H-spiro[benzo[fg]cyclopenta[a]anthracene-9,6'-cyclopenta[a]phenanthrene]-3,17'-diyl diacetate ("dimer-2").

$^1$H NMR (CDCl$_3$, 799.7 MHz) δ: 5.93 (s, 1H), 3.63 (br s, 1H), 2.89-3.01 (m, 2H), 2.55 (dd, J=18.5, 5.5 Hz, 1H), 2.28-2.40 (m, 2H), 2.15-2.23 (m, 1H), 2.11 (s, 3H), 2.11 (s, 3H), 2.06 (s, 3H), 2.05 (s, 3H), 1.92-2.08 (m, 6H), 1.81-1.92 (m, 8H), 1.61-1.80 (m, 9H), 1.54-1.60 (m, 3H), 1.46-1.54 (m, 1H), 1.26-1.35 (m, 5H), 1.20-1.25 (m, 1H), 0.86 (dd, J=13.0, 11.4 Hz, 1H), 0.69 (s, 3H), 0.66 (s, 3H)

$^{13}$C NMR (CDCl$_3$, 201.1 MHz) δ: 209.0, 204.1, 203.9, 199.3, 174.3, 170.7, 170.6, 130.1, 126.2, 121.6, 96.8, 96.6, 54.7, 51.3, 50.8, 47.3, 47.1, 46.8, 43.6, 43.3, 43.2, 41.1, 40.9, 40.4, 38.3, 37.1, 36.4, 33.7, 31.3, 31.1, 30.9, 30.5, 30.2, 26.5, 26.5, 26.2, 25.6, 24.0, 23.7, 23.7, 23.5, 21.2, 14.8, 14.4

HRMS: 741.43673 (C$_{46}$H$_{61}$O$_8$; calc. 741.43610). ESI-MS-MS (rel. int %, cid=35%): 723(100); 681(9); 663(2); 639(1); 621(4); 603(1); 579(1); 371(14).

The ethyl acetate solution, obtained above after the removal of the Nomegestrol-acetate-dimer-2 was concentrated and the obtained dry residue was purified by column chromatography using 150 g of silica gel and a mixture of dichloromethane and acetone as solvent. The fractions containing the product were concentrated and the dry residue was recrystallized from diethyl ether. (TLC: dichloromethane-acetone=9:1, Rf value: dimer-1: 0.5; dimer-2: 0.38; starting material: 0.62). After drying 0.41 g of a product was obtained, which according to structure elucidation was (3R,3aS,5aS,5bR,8'R,8aR,9R,9'S,10'R,12aR,12bS,13'S,14'S,17'R)-3,17'-diacetyl-3a,13'-dimethyl-3',8-dioxo-1',2,2',3,3',3a,4,5,5a,5b,6,7,7',8,8',8a,9',10,10',11,11',12,12',12a,12b,13',14',15',16',17'-triacontahydro-1H-spiro[benzo[fg]cyclopenta[a] anthracene-9,6'-cyclopenta[a]phenanthrene]-3,17'-diyl diacetate ("dimer-1").

$^1$H NMR (CDCl$_3$, 799.7 MHz) δ: 5.97 (s, 1H), 3.46 (br s, 1H), 2.93 (ddd, J=15.9, 11.4, 2.3 Hz, 1H), 2.88 (ddd, J=15.8, 11.4, 2.1 Hz, 1H), 2.74 (br d, J=12.2 Hz, 1H), 2.44-2.51 (m, 1H), 2.27-2.43 (m, 5H), 2.03-2.19 (m, 3H), 2.11 (s, 3H), 2.10 (s, 3H), 2.05 (s, 3H), 2.04 (s, 3H), 1.95-2.03 (m, 5H), 1.88-1.94 (m, 2H), 1.66-1.83 (m, 8H), 1.52-1.59 (m, 3H), 1.38-1.45 (m, 1H), 1.26-1.37 (m, 5H), 1.13-1.26 (m, 2H), 0.89-0.95 (m, 1H), 0.87 (t, J=12.8 Hz, 1H), 0.66 (s, 3H), 0.64 (s, 3H)

$^{13}$C NMR (CDCl$_3$, 201.1 MHz) δ: 209.3, 204.1, 204.0, 200.1, 170.7, 170.6, 131.0, 128.2, 121.5, 96.8, 96.5, 50.7, 50.3, 48.6, 47.1, 47.0, 45.7, 44.1, 42.9, 42.8, 41.9, 39.7, 36.8, 36.2, 35.6, 33.8, 32.6, 31.0, 30.9, 30.4, 30.2, 27.7, 27.1, 26.6, 26.5, 26.4, 24.6, 23.6, 23.5, 21.2, 21.2, 14.5, 14.4

HRMS: 371.22170 (C$_{23}$H$_{31}$O$_4$; calc. 371.22169). ESI-MS-MS (rel. int %, cid=35%): 311(100); 293(12); 275(3); 269(4); 267(2); 251(7); 235(2); 209(7).

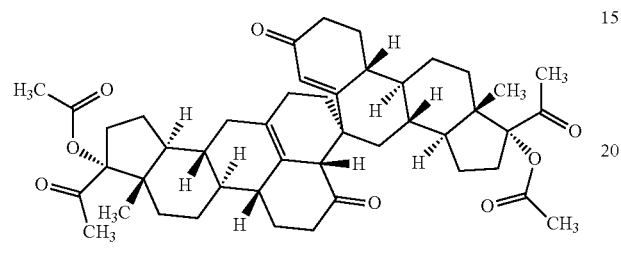

dimer-2

(3R,3aS,5aS,5bR,8'R,8aR,9S,9'S,10'R,12aR,12bS,13'S,14'S,17'R)-3,17'-diacetyl-3a,13'-dimethyl-3',8-dioxo-1',2,2',3,3',3a,4,5,5a,5b,6,7,7',8,8',8a,9',10,10',11,11',12,12',12a,12b,13',14',15',16',17'-triacontahydro-1H-spiro[benzo[fg]cyclopenta[a]anthracene-9,6'-cyclopenta[a]phenanthrene]-3,17'-diyldiacetate

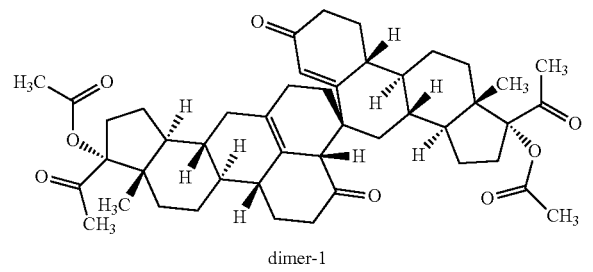

dimer-1

(3R,3aS,5aS,5bR,8'R,8aR,9R,9'S,10'R,12aR,12bS,13'S,14'S,17'R)-3,17'-diacetyl-3a,13'-dimethyl-3',8-dioxo-1',2,2',3,3',3a,4,5,5a,5b,6,7,7',8,8',8a,9',10,10',11,11',12,12',12a,12b,13',14',15',16',17'-tracontahydro-1H-spiro[benzo[fg]cyclopenta[a]anthracene-9,6'-cyclopenta[a]phenanthrene]-3,17'-diyldiacetate

The invention claimed is:

1. A process for the synthesis of Nomegestrol-acetate of formula (I)

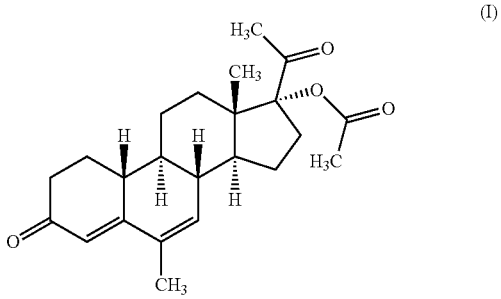

characterized by
adding the solid starting steroid of formula (II)

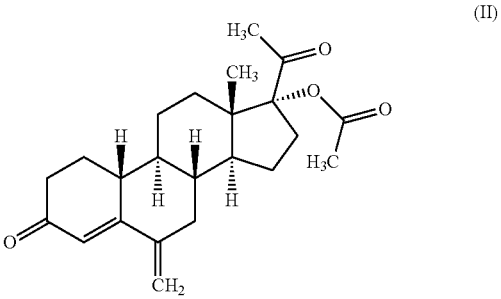

into an ethanolic solution at 50-78° C., which contains 0.05-0.2 mass fraction of 10% Pd/C catalyst, and 0.01-0.2 mass fraction of acetic acid calculated on the weight of the starting steroid of formula (II), then, after 3-15 min reaction time the catalyst is filtered off, the filtrate is concentrated to one fourth in vacuum, water is added to residue and the precipitated product of formula (I) is filtered off at 0-25° C.

2. The process according to claim 1, characterized by using 0.08-0.12 mass fraction of catalyst.

3. The process according to claim 1, characterized by using 0.03-0.07 mass fraction of acetic acid in the reaction.

4. The process according to claim 1, characterized by carrying out the reaction for 5-10 min.

5. The process according to claim 1, characterized by using 10-100 fold volume of ethanol calculated on the weight of the steroid.

6. The process according to claim 1, characterized by carrying out the reaction at 70-78° C.

7. The process according to claim 1, characterized by using 20-40 fold volume ethanol calculated on the weight of the steroid.

* * * * *